United States Patent
Foster

(10) Patent No.: US 6,333,342 B1
(45) Date of Patent: Dec. 25, 2001

(54) METHODS OF PHARMACOLOGICAL TREATMENT USING S(–) AMLODIPINE

(75) Inventor: Robert T. Foster, Edmonton (CA)

(73) Assignee: Isotechnika, INC, Edmonton (CA)

(*) Notice: Subject to any disclaimer, the term of this patent is extended or adjusted under 35 U.S.C. 154(b) by 0 days.

(21) Appl. No.: 09/433,963

(22) Filed: Nov. 4, 1999

Related U.S. Application Data

(60) Provisional application No. 60/107,007, filed on Nov. 4, 1998.

(51) Int. Cl.$^7$ ............... A61K 31/44; C07D 213/80; C07D 213/803
(52) U.S. Cl. ............................ 514/356; 546/321
(58) Field of Search ............................ 514/356

(56) References Cited

U.S. PATENT DOCUMENTS 5,750,707 * 5/1998 Spargo ................. 546/321
5,846,514 * 12/1998 Foster et al. ................. 424/1.81

FOREIGN PATENT DOCUMENTS

9310779 * 6/1993 (WO) .

* cited by examiner

*Primary Examiner*—Theodore J. Criares
*Assistant Examiner*—Jennifer Kim
(74) *Attorney, Agent, or Firm*—Burns, Doane, Swecker & Mathis, L.L.P.

(57) ABSTRACT

Methods and compositions are disclosed utilizing the optically pure S(–) isomer of amlodipine. This compound is a potent drug for the treatment of hypertension while avoiding the concomitant liability of adverse effects associated with the administration of the racemic mixture of amlodipine. The S(–) isomer of amlodipine is also useful for the treatment of angina and such other conditions as may be related to the activity of S(–) amlodipine as a calcium channel antagonist without the concomitant liability of adverse effects associated with the racemic mixture of amlodipine.

4 Claims, No Drawings

METHODS OF PHARMACOLOGICAL TREATMENT USING S(−) AMLODIPINE

This application claims benefit of Prov. No. 60/107,007 filed Nov. 4, 1998.

BACKGROUND OF THE INVENTION

Pharmacological therapy utilizing pure formulations of S(−) amlodipine results in effective theraputic results while avoiding toxicities and adverse effects of racemic amlodipine. The methods and compositions described include the enriched deuterated forms of amlodipine as well as the nonenriched form. Amlodipine and deuteroamlodipine have a chiral center at C4 in the dihydropyridine ring, and thus can exist as optical isomers. The isomers may be separated by various methods, for example selective crystallization and column chromatography. See for example T. Shibanuma, et al., *Chem. Pharm. Bull.*, 28, 2809–2812 (1980). Alternatively, S(−) amlodipine may be prepared using optically active reactants, or by a combination of separation and chiral synthesis. Optical isomers of compounds are specified (+) or (−), indicating the direction the chiral center rotates a plane of polarized light.

Optically active amlodipine, amlodipine derivatives and salts and deuterated amlodipine or deuterated amlodipine derivatives and salts are designated herein using the IUPAC R-S convention, sometimes called the "sequence rule." A description of the R-S convention may be found, for example, in "Introduction to Organic Chemistry" by A. Streitwieser, Jr. and C. Heathcock, (Macmillan Pub. Co., New York, 1976), pages 110–114.

Optical purity is important since certain isomers may actually be deleterious rather than simply inert. For example, it has been suggested that the D-enantiomer of thalidomide was a safe and effective sedative when prescribed for the control of morning sickness during pregnancy, while the corresponding L-enantiomer has been thought to be a potent teratogen.

The active compound of the present invention is the S(−) isomer of the compound amlodipine and the s(−) isomer of deuterated amlodipine. Amlodipine is described in U.S. Pat. No. 4,572,909. Chemically, this compound is the S(−) isomer of amlodipine and is a long-acting calcium channel blocker.

Amlodipine is chemically described as (R.S.) 3-ethyl-5-methyl-2-(2-aminoethoxymethyl)-4-(2-chlorophenyl)-1,4-dihydro-6-methyl-3,5-pyridinedicarboxylate. Its empirical formula is: $C_2OH_{25}ClN_2O_5$. Also encompassed within the present invention are compositions and methods of using deuterated compounds which are related to amlodipine. In the structures given below, R represents either hydrogen or deuterium. In a preferred embodiment, $R^1$ represents either hydrogen or deuterium wherein one or more $R^1$ is deuterium. The symbol "*" denotes the chiral carbon.

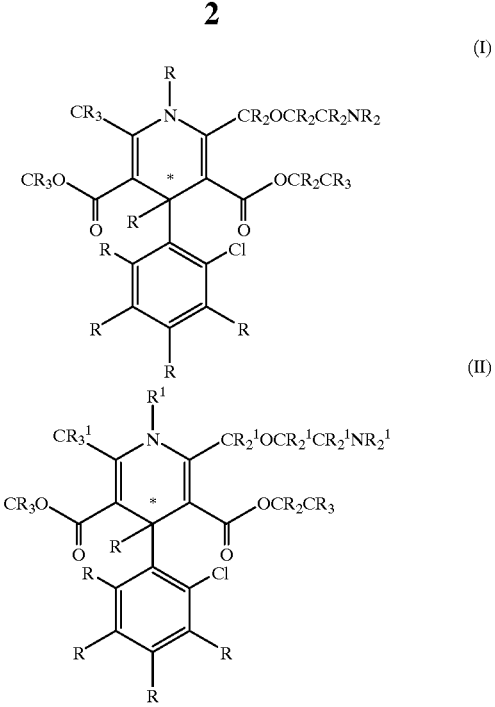

The present commercial formulation of amlodipine contains the drug as the salt; amlodipine besylate. The term "amlodipine" herein refers to amlodipine and its pharmaceutically suitable salts and esters including amlodipine besylate and deuterated amlodipine and its pharmaceutically acceptable salts and esters including deuterated amlodipine besylate. This isomer will hereinafter be referred to as S(−) amlodipine. The terms "S(−) amlodipine" and "S(−) isomer of amlodipine" as used herein includes substantially optically pure S(−) amlodipine as well as optically pure S(−) amlodipine.

Pharmacological Action of Amlodipine

Mechanism of Action:

Amlodipine is a dihydropyridine calcium antagonist (calcium ion antagonist or slow channel blocker) that inhibits the transmembrane influx of calcium ions into vascular smooth muscle and cardiac muscle. Experimental data suggest that amlodipine binds to both dihydropyridine and nondihydropyridine binding sites. The contractile processes of cardiac muscle and vascular smooth muscle are dependent upon the movement of extracellular calcium ions into these cells through specific ion channels. Amlodipine inhibits calcium ion influx across cell membranes selectively, with a greater effect on vascular smooth muscle cells than on cardiac muscle cells. The (−) isomer has been reported to be more active than the (+) isomer. Negative inotropic effects can be detected in vitro but such effects have not been seen in intact animals at therapeutic doses. Serum calcium concentration is not affected by amlodipine. Within the physiologic pH range, amlodipine is an ionized compound (pKa=8.6), and its kinetic interaction with the calcium channel receptor is characterized by a gradual rate of association and dissociation with the receptor binding site, resulting in a gradual onset of effect.

Amlodipine is a peripheral arterial vasodilator that acts directly on vascular smooth muscle to cause a reduction in peripheral vascular resistance and reduction in blood pressure.

The precise mechanisms by which amlodipine relieves angina have not been fully delineated, but are thought to include the following:

Exertional Angina: In patients with exertional angina, amlodipine reduces the total peripheral resistance (afterload) against which the heart works and reduces the rate pressure product, and thus myocardial oxygen demand, at any given level of exercise.

Vasospastic Angina: Amlodipine has been demonstrated to block constriction and restore blood flow in coronary arteries and arterioles in response to calcium, potassium epinephrine, serotonin, and thromboxane A2 analog in experimental animal models and in human coronary vessels in vitro. This inhibition of coronary spasm is responsible for the effectiveness of amlodipine in vasospastic (Prinzmetal's or variant) angina.

Pharmacokinetics and Metabolism:

After oral administration of therapeutic doses of amlodipine, absorption produces peak plasma concentrations between 6 and 12 hours. Absolute bioavailability has been estimated to be between 64 and 90%. The bioavailability of amlodipine is not altered by the presence of food.

Amlodipine is extensively (about 90%) converted to inactive metabolites via hepatic metabolism with 10% of the parent compound and 60% of the metabolites excreted in the urine. Ex vivo studies have shown that approximately 93% of the circulating drug is bound to plasma proteins in hypertensive patients. Elimination from the plasma is biphasic with a terminal elimination half-life of about 30–50 hours. Steady state plasma levels of amlodipine are reached after 7 to 8 days of consecutive daily dosing.

The pharmacokinetics of amlodipine are not significantly influenced by renal impairment. Patients with renal failure may therefore receive the usual initial dose.

Elderly patients and patients with hepatic insufficiency have decreased clearance of amlodipine with a resulting increase in AUC of approximately 40–60%, and a lower initial dose may be required.

Pharmacodynamics:

Hemodynamics: Following administration of therapeutic doses to patients with hypertension, amlodipine produces vasodilation resulting in a reduction of supine and standing blood pressures. These decreases in blood pressure are not accompanied by a significant change in heart rate or plasma catecholamine levels with chronic dosing. Although the acute intravenous administration of amlodipine decreases arterial blood pressure and increases heart rate in hemodynamic studies of patients with chronic stable angina, chronic administration of oral amlodipine in clinical trials did not lead to clinically significant changes in heart rate or blood pressures in normotensive patients with angina.

With chronic once daily oral administration, antihypertensive effectiveness is maintained for at least 24 hours. Plasma concentrations correlate with effect in both young and elderly patients. The magnitude of reduction in blood pressure with amlodipine is also correlated with the height of pretreatment elevation; thus, individuals with moderate hypertension (diastolic pressure 105–114 mmHg) had about a 50% greater response than patients with mild hypertension (diastolic pressure 90–104 mmHg). Normotensive subjects experienced no clinically significant change in blood pressures (+1/-2 mmHg).

As with other calcium channel blockers, hemodynamic measurements of cardiac function at rest and during exercise (or pacing) in patients with normal ventricular function treated with amlodipine have generally demonstrated a small increase in cardiac index without significant influence on dP/dt or on left ventricular end diastolic pressure or volume. In hemodynamic studies, amlodipine has not been associated with a negative inotropic effect when administered in the therapeutic dose range to intact animals and man, even when co-administered with beta-blockers to man. Similar findings, however, have been observed in normals or well-compensated patients with heart failure with agents possessing significant negative inotropic effects.

In a double-blind, placebo-controlled clinical trial involving 118 patients with well compensated heart failure (NYHA Class II and Class III), treatment with amlodipine did not lead to worsened heart failure, based on measures of exercise tolerance, left ventricular ejection fraction and clinical symptomatology. Studies in patients with NYHA Class IV heart failure have not been performed and, in general, all calcium channel blockers should be used with caution in any patient with heart failure.

In hypertensive patients with normal renal function, therapeutic doses of amlodipine resulted in a decrease in renal vascular resistance and an increase in glomerular filtration rate and effective renal plasma flow without change in filtration fraction or proteinuria.

Electrophysiologic Effects:

Amlodipine does not change sinoatrial nodal function or atrioventricular conduction in intact animals or man. In patients with chronic stable angina, intravenous administration of 10 mg did not significantly alter A-H and H-V conduction and sinus node recovery time after pacing. Similar results were obtained in patients receiving amlodipine and concomitant beta blockers. In clinical studies in which amlodipine was administered in combination with beta-blockers to patients with either hypertension or angina, no adverse effects on electrocardiographic parameters were observed. In clinical trials with angina patients alone, amlodipine therapy did not alter electrocardiographic intervals or produce higher degrees of AV blocks.

Effects in Hypertension:

The antihypertensive efficacy of amlodipine has been demonstrated in a total of 15 double-blind, placebo-controlled, randomized studies involving 800 patients on amlodipine and 538 on placebo. Once daily administration produced statistically significant placebo-corrected reductions in supine and standing blood pressures at 24 hours postdose, averaging about 12/6 mmHg in the standing position and 13/7 mmHg in the supine position in patients with mild to moderate hypertension. Maintenance of the blood pressure effect over the 24 hour dosing interval was observed, with little difference in peak and trough effect. Tolerance was not demonstrated in patients studied for up to 1 year. The 3 parallel, fixed dose, dose response studies showed that the reduction in supine and standing blood pressures was dose-related within the recommended dosing range. Effects on diastolic pressure were similar in young and older patients. The effect on systolic pressure was greater in older patients, perhaps because of greater baseline systolic pressure. Effects were similar in black and white patients.

Effects in Chronic Stable Angina:

The effectiveness of 5–10 mg/day of amlodipine in exercise-induced angina has been evaluated in 8 placebo-controlled, double-blind clinical trials of up to 6 weeks duration involving 1038 patients (648 amlodipine, 354 placebo) with chronic stable angina. In 5 of the 8 studies significant increases in exercise time (bicycle or treadmill) were seen with the 10 mg dose. Increases in symptom-limited exercise time averaged 12.8% (63 sec) for amlodipine 10 mg, and averaged 7.9% (38 sec) for amlodipine 5 mg. Amlodipine 10 mg also increased time to 1 mm ST segment deviation in several studies and decreased angina attack rate. The sustained efficacy of amlodipine in angina patients has been demonstrated over long-term dosing. In patients with angina there were no clinically significant reductions in blood pressures (4/1 mmHg) or changes in heart rate (+0.3 bpm).

Effects in Vasospastic Angina:

In a double-blind, placebo-controlled clinical trial of 4 weeks duration in 50 patients, amlodipine therapy decreased attacks by approximately 4/week compared with a placebo decrease of approximately 1/week (p<0.01). Two of 23 amlodipine and 7 of 27 placebo patients discontinued from the study due to lack of clinical improvement.

Amlodipine is presently administered and is available commercially only as the 1:1 racemic mixture. That is, it is available as a mixture of optical isomers, called enantiomers. As stated above, enantiomers are structurally identical compounds which differ only in that one isomer is a mirror image of the other and the mirror images cannot be superimposed. This phenomenon is known as chirality.

Dihydropyridine calcium channel blockers are also known as calcium antagonists. The concept of a specific mechanism of pharmacologic action related to the antagonism of calcium movement in the process of excitation-contraction was suggested by Fleckenstein et. al. See *Calcium Antagonism in Heart and Smooth Muscle:Experimental Facts and Therapeutic Prospects*, New York, Wiley, 1983. (See also Swamy, V. and D. Triggle, *Modern Pharmacology*, 2nd. Ed., Craig and Stitzel, Eds., Little, Brown and Co., Boston, 1986, Chapt. 26, 373–380; and Triggle, D. J., and R. A. Janis, *Ann. Rev. Pharm. and Tox.* 27: 347–369, 1987). Many of the currently available calcium antagonists appear to antagonize the entry of calcium through voltage dependent channels in the plasma membrane of cells. The pharmacologic class of calcium antagonists consists of chemically diverse compounds. Given the structural heterogeneity of the class it is likely that the pharmacological action involves more than one site or mechanism of action.

Amlodipine is one of a series of dihydropyridine calcium antagonists. Its ability to block calcium channels in smooth muscle produces peripheral vasodilation resulting in decreases in both systolic and diastolic blood pressure in hypertensive animals and humans.

Calcium Uptake Inhibiting Activity

Cellular calcium flux is regulated by receptor-operated and voltage-dependent channels which are sensitive to inhibition by calcium entry blockers. The term calcium antagonist was introduced by Fleckenstein (1964,1967) when two drugs, prenylamine and verapamil, originally found as coronary dilators in the LANGENDORFF-experiment, were shown to mimic the cardiac effects of simple $Ca^{++}$-withdrawal, diminishing $Ca^{++}$-dependent high energy phosphate utilization, contractile force, and oxygen requirement of the beating heart without impairing the $Na^+$-dependent action potential parameters. These effects were clearly distinguishable from b-receptor blockade and could promptly be neutralized by elevated $Ca^{++}$, $\beta$-adrenergic catecholamines, or cardiac glycosides, measures that restore the $Ca^{++}$ supply to the contractile system. In the following years many $Ca^{++}$-antagonists were introduced to therapy. Specific $Ca^{++}$-antagonists interfere with the uptake of $Ca^{++}$ into the myocardium and prevent myocardial necrotization arising from deleterious intracellular $Ca^{++}$ overload. They act basically as specific inhibitors of the slow transsarcolemnal $Ca^{++}$ influx but do not or only slightly affect the fast $Na^+$ current that initiates normal myocardial excitation.

Calcium channels and the sites of action of drugs modifying channel function have been classified (Bean 1989, Porzig 1990, Tsien and Tsien 1990, Spedding and Paoletti 1992). Four main types of voltage dependent calcium channels are described: L type (for long lasting), T type (for transient), N type (for neuronal), and P type (for Purkinje cells). They differ not only by their function (Dolphin 1991) and localization in tissues and cells but also by their sensitivity to pharmacological agents (Ferrante and Triggle 1990, Dascal 1990) and by their specificity to radioligands. The widely distributed L type channels exist in isoforms (L1, 2, 3, 4) and consist of several subunits, known as $\alpha_1$, $\alpha_2$, $\beta$, $\gamma$, $\delta$. They are sensitive to dihydropyridines, phenylalkylamines or benzothiazepines, but insensitive to $\omega$-conotoxin and $\omega$-agatoxin. The T type channels are located mainly in the cardiac sinoatrial node and have different electrophysiological characteristics from L type channels. N-and P-type calcium channels blockers occur in neuronal cells and are involved in neurotransmitter release (Bertolino and Llinas 1992, Mintz et al 1992). Up to now, there are no highly selective blockers of T-, N-, and P-channels with potential therapeutic applications.

The racemic mixture of amlodipine is presently used primarily as an antihypertensive agent, and it is generally taken orally as a once-daily therapy. Pharmacologic management of hypertension is generally directed to the normalization of altered hemodynamic parameters, and many drugs and drug classes, either as monotherapy or in combination treatment, can reduce and control elevated blood pressure.

Furthermore, the racemic mixture of amlodipine is useful in treating other disorders such as angina pectoris. Angina pectoris is a clinical syndrome reflecting myocardial ischemia. A condition where cardiac work or myocardial oxygen demand exceeds the ability of the coronary arterial vascular system to supply oxygen results in myocardial ischemia, which may cause either a painful angina attack or an angina attack that is not accompanied by pain (silent ischemia). Under extreme circumstances, the lack of oxygen may cause a myocardial infarction or cardiac arrhythmias. The treatment of angina is directed to the underlying disease, usually atherosclerosis, or to drugs which either reduce myocardial oxygen demand or improve oxygen supply. Calcium antagonists such as amlodipine have been particularly useful in treating vasospastic angina, the angina of effort, and the unstable angina, due to the effect of the calcium channel antagonist on cardiac and vascular smooth muscle.

Amlodipine may be useful in the treatment of cerebral ischemia. Cerebral ischemia, often the result of atherosclerotic disease or hypertension, results from insufficient cerebral circulation. Under normal circumstances, an extensive collateral circulation ensures adequate blood flow. However, cerebral ischemia may result from either an intra- or extracranial interruption of arterial blood flow caused by atherosclerosis or arterial vasoconstriction. If interruption is transient, the cause is usually arterial vasoconstriction and a calcium antagonist may be of therapeutic value. If the ischemia lasts for a more extended period, it is usually caused by carotid or cerebral atherosclerosis that may be accompanied by a vasospecific condition that can be treated with a vasodilating calcium antagonist.

Because of its activity as a calcium channel antagonist, amlodipine may also be useful in treating cardiac arrhythmias. Cardiac arrhythmias represent a broad, complex group of electrophysiologic disorders that effects the mechanical properties of the heart and vasculature, altering normal cardiac rhythm, function and output. Normal cardiac rhythm originates as a calcium dependent action potential within the, sinoatrial node, propagates through the atria and passes as a calcium dependent potential through the atrioventricular node and along the purkinje fibers into the ventricles of the heart. Adequate automaticity and conduction are necessary elements of normal functional heart beat. Calcium antagonists may be of value in conditions where calcium-related changes in membrane potential and conduction alter normal rhythm and in cases of ischemia-induced cardiac arrhythmias.

Amlodipine may be useful to treat cardiac hypertrophy. Cardiac hypertrophy can result from excessive workload either due to an obstruction to outflow, termed systolic overload, or to excessive volumes presented to the heart in diastole, termed diastolic overload. Systolic overload results in concentric ventricular hypertrophy, in which there is an increased thickness in the walls of the heart not associated with increased volume. Diastolic overload causes dilation and hypertrophy with an increased blood volume. An inadequate cardiac output results from the heart's failure in systolic or diastolic overload. Calcium channel antagonists dilate peripheral capacitance blood vessels and thereby reduce the amount of blood returning to the heart and the risk for diastolic overload. Calcium antagonists also dilate peripheral resistance blood vessels, thereby reducing blood pressure (cardiac afterload) and the risk for systolic overload.

Myocardial infarction may be precipitated by coronary artery vasospasm or acute coronary thrombosis. Calcium channel antagonists may find utility in the management of myocardial infarction patients due to "direct" anti-ischemic effects or due to their effects on coronary artery vasospasm, blood pressure or other cardiac or vascular functions.

Amlodipine may be used to treat congestive heart failure. Congestive heart failure can be caused by hypertension, cardiomyopathy, coronary artery disease or valvular heart disease. Congestive failure results in poor cardiac output and elevated left-ventricular diastolic pressure, leading to dyspnea, fatigue, peripheral edema, and coughing. The ability of some calcium antagonists to lower arterial blood pressure by dilating peripheral arteries without having a significant inotropic effect may increase their use in treating congestive heart failure.

Amlodipine may be of use in treating migraine. Classic migraine typically begins with visual auras followed by severe headaches, often accompanied by nausea and vomiting. Common migraine has similar symptoms without the preceding visual aura. The causes of migraine have been studied intensely, and are still a matter of debate. The most generally accepted cause is an initial cerebral vasoconstriction, followed by a cerebral vasodilatation. Calcium channel antagonists have been used for migraine prophylaxis since they can inhibit the initial vasoconstriction.

Amlodipine may also be useful for treating Raynaud's phenomenon, which is characterized by vascular spasm of the extremities. These vasospasms can be caused by cold or stress. A pallor or cyanosis is usually present due to severe constriction of the digital arteries. The phenomenon is often seen as a secondary disorder with arterial diseases or connective tissue diseases such as scleroderma, arthritis or lupus erythematosus. Calcium channel antagonists have been shown to be effective in treating Raynaud's phenomenon.

Amlodipine may be useful in the treatment of asthma and bronchospasm. Symptoms of asthma-coughing, wheezing, and dyspnea-are caused by constriction of tracheobronchial smooth muscle. Asthma attacks can be triggered by antigenic stimuli (pollen, dust) or non-antigenic stimuli (exercise, pollution, infection). The response to these stimuli lead to secretions of chemical mediators that cause smooth muscle contraction. Calcium channel antagonists can cause relaxation of the bronchial smooth muscles and thereby relieve or prevent asthma attacks.

The racemic mixture of amlodipine may be useful to treat renal impairment and acute renal failure. Renal impairment and acute renal failure are clinical conditions of diverse etiology, which are associated with an increasing azotemia or urea nitrogen in the blood, and often an oliguria or a diminished volume of urine in relation to fluid intake. The pathophysiology may originate prerenally, manifest as inadequate renal perfusion, due to extracellular fluid volume depletion or cardiac failure. The most common cause of intrinsic renal failure is prolonged renal ischemia. Postrenal azotemia may be associated with obstruction or renal glomerular and tubular dysfunction. Laboratory findings in patients with renal failure often disclose progressive azotemia, acidosis, hyperkalemia, and hyponatremia. Factors aggravating kidney impairment or failure must be specifically treated, including heart failure, obstruction and the like. Moderate or severe hypertension has a deleterious effect on renal function, and management of the hypertension with a variety of drugs including calcium channel antagonists may be useful therapy.

In addition, the racemic mixture of amlodipine could be useful in the treatment of cognitive disorders. Cognitive disorders include but are not limited to dementia and age-associated memory impairment.

Calcium antagonists such as amlodipine may also be used for the treatment of ocular (retinal) ischemia, that often is the result of local vasoconstriction.

Many calcium channel antagonists cause significant adverse effects. These adverse effects include but are not limited to tachycardia, orthostatic hypotension, fluid retention and insulin resistance. The administration of the racemic mixture of amlodipine to a human has been found to cause still other adverse effects. These adverse effects include but are not limited to headache and edema, dizziness, flushing, palpitation, fatigue, nausea, abdominal pain and somnolence.

SUMMARY OF THE INVENTION

The methods and compositions of the present invention utilize the discovery that the optically pure S(-) isomer of amlodipine is an effective antihypertensive agent for both systolic and diastolic hypertension, particularly in mild to moderate disease and angina, which avoids the adverse effects including but not limited to headache and edema, dizziness, flushing, palpitation, fatigue, nausea, abdominal pain and somnolence which are associated with the administration of the racemic mixture of amlodipine. It has also been discovered that these novel compositions of matter containing optically pure S(-) amlodipine are useful in treating other conditions as may be related to the activity of S(-) amlodipine as a calcium channel antagonist, including but not limited to cerebral ischemia, cerebral disorders, arrhythmias, cardiac hypertrophy, heart failure, coronary vasospasm, myocardial infarction, renal impairment, viral infection, thrombosis, atherosclerosis, peripheral vascular disease, migraine headache, restenosis following vascular surgery or injury and acute renal failure while avoiding the above-described adverse effects associated with the administration of the racemic mixture of amlodipine. The present invention also includes methods for treating the above-described conditions in a human while avoiding the adverse effects that are associated with the racemic mixture of amlodipine by administering the S(−) isomer of amlodipine to said human.

The present invention relates to a method of treating hypertension in an individual, comprising administering to the individual a therapeutically effective amount of the optically pure S(−) enantiomer of amlodipine which has calcium channel blocking activity. The optically pure S(−) enantiomer is substantially free of the R(+) enantiomer which lacks or has a lower level of such activity. The present method is useful in treating hypertension while reducing or avoiding undesirable adverse effects, such as headache and edema, dizziness, flushing, palpitation, fatigue, nausea, abdominal pain and somnolence which are often associated with administration of a racemic mixture of amlodipine. In these applications, it is important to have an calcium channel blocking composition which minimize these side effects. A composition containing the optically pure S(−) isomer of amlodipine having calcium channel blocking activity is particularly useful for this application because the S(−) isomer exhibits both of these desired characteristics.

The present method provides a safe, highly effective method for treating severe hypertension while reducing undesirable adverse effects associated with anti-hypertensive drugs, including the racemic mixture of amlodipine.

DETAILED DESCRIPTION OF THE INVENTION

The present invention encompasses a method of treating hypertension in a human while avoiding the concomitant liability of adverse effects associated with the racemic mixture of amlodipine, which comprises administering to a human in need of such anti-hypertensive therapy, an amount of S(−) amlodipine or a pharmaceutically acceptable salt thereof, substantially free of its R(+) stereoisomer, said amount being sufficient to alleviate hypertension, but insufficient to cause said adverse effects associated with administration of racemic amlodipine.

The present invention also encompasses an pharmaceutical composition for treatment of hypertension, in a human in need of anti-hypertensive therapy, which comprises an amount of S(−) amlodipine or a pharmaceutically acceptable salt thereof, substantially free of its R(+) stereoisomer, said amount being sufficient to alleviate hypertension but insufficient to cause adverse effects of racemic amlodipine. The calcium channel blocking composition may optionally contain a pharmaceutically acceptable carrier.

The present invention further encompasses a method of treating angina in a human, while avoiding the concomitant liability of adverse effects associated with the administration of racemic amlodipine, which comprises administering to a human in need of anti-angina therapy, an amount of S(−) amlodipine, or a pharmaceutically acceptable salt thereof, substantially free of its R(+) stereoisomer, said amount being sufficient to alleviate angina but insufficient to cause said adverse effects associated with administration of racemic amlodipine.

In addition, the present invention encompasses an pharmaceutical composition for the treatment of a human having angina, which comprises an amount of S(−) amlodipine or a pharmaceutically acceptable salt thereof, substantially free of its R(+) stereoisomer, said amount being sufficient to alleviate angina but insufficient to cause adverse effects associated with the administration of racemic amlodipine. The antianginal composition may optionally contain a pharmaceutically acceptable carrier.

A further aspect of the present invention includes a method of treating a condition caused by excessive calcium influx in cells in a human, while avoiding the concomitant liability of adverse effects associated with the administration of racemic amlodipine, which comprises administering to a human in need of a reduction in excessive calcium influx, an amount of S(−) amlodipine, or a pharmaceutically acceptable salt thereof, substantially free of its R(+) stereoisomer, said amount being sufficient to alleviate or prevent excessive calcium influx in cells but insufficient to cause said adverse effects associated with the administration of racemic amlodipine. Conditions caused by excessive calcium influx in cells in a human include, but are not limited to, cerebral ischemia, cerebral disorders such as cognitive disorders including but not limited to Alzheimer's dementia and memory impairment, retinal ischemia, viral infection, thrombosis, athersclerosis, arrhythmias, cardiac hypertrophy, congestive heart failure, coronary vasospasm, migraine, bronchospasm and asthma, Raynaud's phenomenon, myocardial infarction, renal impairment, restenosis following vascular surgery or injury and acute renal failure.

The invention also includes a pharmaceutical composition for treating a condition caused by excessive calcium influx in cells in a human, which comprises an amount of S(−) amlodipine, or a pharmaceutically acceptable salt thereof, substantially free of its R(+) stereoisomer, said amount being sufficient to alleviate said condition but insufficient to cause adverse effects associated with the administration of racemic amlodipine. This pharmaceutical composition may optionally contain a pharmaceutically acceptable carrier.

The presently sold commercial preparation of amlodipine besylate is a racemic mixture of amlodipine (e.g., a 1:1 racemic mixture of the two enantiomers) and demonstrates antihypertensive and antianginal activity. The racemic mixture of amlodipine causes adverse effects. Utilizing the optically pure S(−) isomer of amlodipine results in clearer dose-related definitions of efficacy, surprisingly diminished adverse effects, and accordingly, an improved therapeutic index. It is, therefore, more desirable to use the optically pure S(−) isomer of amlodipine.

The terms "patient" and "animal" are intended to encompass mammalian species including but not limited to humans.

The term "adverse effects of racemic amlodipine" or "adverse effects associated with the racemic mixture of amlodipine as used herein includes, but is not limited to, headache and edema, dizziness, flushing, palpitation, fatigue, nausea, abdominal pain and somnolence.

The term "substantially free of its R(+) stereoisomer" as used herein means that the composition contains a greater proportion or percentage of the S(−) isomer of amlodipine in relation to the R(+) isomer of amlodipine, said percentage being based on the total amount of amlodipine in the composition. In a preferred embodiment the term "substantially free of its R(+) stereoisomer" means that the composition contains at least 90% by weight of S(−) amlodipine, and 10% by weight or less of R(+) amlodipine. In the most preferred embodiment the term "substantially free of the R(+) stereoisomer" means that the composition contains at least 99% by weight S(−) amlodipine, and 1% or less of R(+) amlodipine. In another preferred embodiment the term "substantially free of its R(+) stereoisomer" as used herein means that the composition contains about 100% by weight of S(−)

amlodipine. The terms "substantially optically pure S(−) isomer of amlodipine" and "optically pure S(−) isomer of amlodipine" are also encompassed by the above-described meanings.

The term "a method of treating hypertension" as used herein means providing a normalization to otherwise elevated systolic and/or diastolic blood pressure, and by so doing providing relief from any possible symptoms or other hemodynamic effects caused by the elevated pressure.

The term "a method of treating angina" as used herein means relief from the symptoms of myocardial ischemia, which include, but are not limited to, episodes of precordial pressure, discomfort, or a severe intense, crushing pain which may radiate, and which may be accompanied by changes in respiration, pulse rate, and blood pressure.

The term "a condition caused by excessive calcium influx in cells in a human" includes but is not limited to conditions involving calcium influx in human cell that may be present in smooth muscle, cardiac, and other tissues including lung and brain. These conditions include, but are not limited to, cerebral ischemia, cerebral disorders such as cognitive disorders including Alzheimer's dementia and memory impairment, retinal ischemia, arrhythmias, cardiac hypertrophy, congestive heart failure, coronary vasospasm, migraine, bronchospasm and asthma, Raynaud's phenomenon, myocardial infarction, renal impairment and acute renal failure. The symptoms associated with these disorders include, but are not limited to, the symptoms of precordial discomfort or pain, headache, fatigue, decreased exercise tolerance, syncope, shortness of breath, nausea, lightheadedness, edema, pulmonary congestion, arrhythmia or palpitation, azotemia, and/or oliguria.

Optically pure S(−) amlodipine can be prepared in a number of ways. Among these methods, the resolution of a racemic mixture of amlodipine or its precursors and the asymmetric synthesis of amlodipine or precursors thereof are particularly useful. Resolution of a racemic mixture by fractional crystallization of diastereomeric derivatives or salts is perhaps the most straightforward method for obtaining optically pure S(−) amlodipine.

Optically active resolving agents are employed in the resolution of these racemic mixtures of the amlodipine enantiomers which are obtained following synthetic procedures known in the art (See, for example, U.S. Pat. No. 3,799,934.). The resolution of racemates by fractional crystallization of diastereomeric salts formed with such resolving agents is perhaps the most commonly used conventional technique for producing optically pure compounds. See, for example, "Stereochemistry of Carbon Compounds," E. L. Eliel (McGraw-Hill, NY, 1986) and "S. H. Wilen, p. 268, in "Tables of Resolving Agents and Optical Resolutions," E. L. Eliel, Ed., Univ. of Notre Dame Press, Notre Dame, Ind., 1972.

Amlodipine is a basic compound and therefore diastereomeric salts suitable for separation by fractional crystallization are readily formed by the addition of chiral acid resolving agents in optically pure form to racemic amlodipine. Suitable resolving agents for use here include optically pure tartaric acid and its derivatives, camphorsulfonic acid, mandelic acid and derivatives thereof, and other optically active acids. The desired S(−) amlodipine isomer may be recovered either from the crystallized diastereomer or from the mother liquor, depending on the solubility properties of the particular acid resolving agent employed and depending on the particular acid enantiomer used. The identity of the S(−) amlodipine isomer so obtained may be confirmed by polarimetry and other analytical methods.

A particular preferred means of obtaining S(−) amlodipine is based on the fractional crystallization of diastereomeric mixtures formed by basic resolving agents and racemic carboxylic-acid-containing precursors of amlodipine. See, for example, T. Shibanuma et al., *Chem. Pharm. Bull.* 28(9): 2809–2812 (1980) (who resolved the structurally related dihydropyridine nicardipine) and M. Eltze et al., Chirality 2: 233–240 (1990) and references cited therein. In particular, S(−) amlodipine is obtained by means of resolution of the corresponding racemic 4-aryl-l-ethoxymethyl-1,4-dihydro-5-methoxycarbonyl-2,6-dimethylpyridine-3-carboxylic acids by means of crystallization of the diastereomeric salts formed upon addition of basic resolving agents to the racemic precursor-followed by subsequent alkylation and esterification as described in International Patent Applications WO 88/07524 and WO 88/07525, Byk Gulden, 1988. Optically pure cinchonine and cinchonidine salts are basic resolving agents that have proven useful in the resolution of the dihydropyridines including amlodipine.

The chemical synthesis of the racemic mixture of amlodipine can be performed by the method described in U.S. Pat. No. 4,572,909 and 5,438,145 as well as by other means known to those skilled in the art. The racemic acid ester is converted to its cinchonidine salt in methanol solution. Upon dilution with water and standing at room temperature, a crystalline precipitate is formed which can be subsequently recrystallized to constant rotation to give the diastereomerically pure cinchonidine salt. Further, the mother liquids from the original crystallization can be reduced in volume and stirred at room temperature, e.g., overnight, to afford a fine precipitate which can also be recrystallized to give the diastereomerically pure cinchonidine salt. The cinchonidine salt is partitioned between ethyl acetate and dilute hydrochloric acid to liberate the enantiomerically pure acid. The acid is then esterified using carbonyldiimidazole (CDI) and ethanolic sodium ethoxide, yielding S(−) amlodipine.

The various terms "an amount sufficient to alleviate hypertension but insufficient to cause said adverse effects associated with the administration of racemic amlodipine", "an amount sufficient to alleviate angina but insufficient to cause said adverse effects associated with the administration of racemic amlodipine" "an amount sufficient to alleviate ocular (retinal) ischemia, but insufficient to cause said adverse effects associated with the administration of racemic amlodipine" and "an amount sufficient to alleviate said condition but insufficient to cause said adverse effects associated with the administration of racemic amlodipine" wherein said condition includes but is not limited to cerebral ischemia, cerebral disorders, arrhythmias, cardiac hypertrophy, coronary vasospasm, myocardial infarction, renal impairment and acute renal failure, are encompassed by the above described dosage amounts and dose frequency schedule.

In one embodiment of the present method, the optically pure S(−) isomer of amlodipine is administered to an individual suffering from hypertension. For example, S(−) amlodipine is administered therapeutically to an individual to reduce or ameliorate hypertension. In another embodiment, optically pure S(−) amlodipine can be administered prophylactically to reduce the probability of occurrence of hypertension.

Any suitable route of administration may be employed for providing the patient with an effective dosage of (−) amlodipine. For example, oral, rectal, parenteral, ocular, subcutaneous, intravenous, intramuscular, transdermal, and the like may be employed. Dosage forms include tablets, troches, dispersions, suspensions, solutions, capsules, patches, and the like.

S(−) amlodipine and its pharmaceutically acceptable salts and esters and deuterated amlodipine and pharmaceutically salts and esters of the present invention can be used to prepare pharmaceutical compositions useful in the treatment of the diseases and conditions discussed above. In these treatment regimens, a therapeutic amount of S(−) amlodipine (salts, esters and deuterated derivatives) can be administered in admixture with a pharmaceutically acceptable non-toxic carrier. A therapeutically effective amount is that amount which, when administered to a mammal in need thereof, is sufficient to effect treatment, as defined above. Thus, the level of the drug in the formulation can vary from about 5 percent weight (%w) to about 95%w of the drug based on the total formulation and about 5%w to 95%w excipient. Preferably the drug is present at a level of about 10%w to about 70%w.

Useful pharmaceutical carriers for the preparation of the pharamaceutical compositions hereof can be solids or liquids. Thus, the compositions can take the form of tablets, pills, capsules, powders, sustained release formulations solutions, suspensions, elixirs, aerosols, and the like. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "Remington's Pharmaceutical Sciences" by E. W. Martin.

In the practice of the above described method of the present invention a therapeutically effective amount of the S(−) amlodipine or a pharmaceutical composition containing same is administered via any of the usual and acceptable methods known in the art, either singly or in combination with other pharmaceutical agents. These compounds or compositions can thus be administered orally, systemically (e.g., transdermally, intranasally or by suppository) or parenterally (e.g., intramuscularly, subcutaneously and intravenously), and can be administered either in the form of solid or liquid dosages including tablets, solutions, suspensions, aerosols, and the like, as discussed in more detail above. It is preferred to administer S(−) amlodipine orally.

The formulation can be administered in a single unit dosage form for continuous treatment or in a single unit dosage form ad libitum when relief of symptoms is specifically required.

The Spontaneously Hypertensive Rat (SHR) assay is an accepted test for determining antihypertensive activity. See, e.g., J. Roba, et al., Arch. Int. Pharmacodyn., 200, 182 (1972).

Other accepted tests for cardiovascular activity include ultrasonic two-dimensional echocardiography and anesthetized dog assays. See, e.g., P. Gueret, M.D., et al., Circulation, 62(6), 1308 (1980), and M. Tripp, American J. of Physiology, 232(2), H173 (1977), respectively.

In view of the foregoing as well as in consideration of the degree of severity of the condition being treated, age of subject and so forth, all of which factors are determinable by routine experimentation by one skilled in the art, the effective dosage in accordance herewith can vary over a wide range. Generally, a therapeutically effective amount ranges from about 1.0 to about 1000 µg/Kg body weight per day and preferably, for example, for antihypertensive use, from about 30 to about 500 µg/Kg body weight per day. In alternative terms, for an average 70 Kg adult human subject, a therapeutically effective amount in accordance herewith would be, in preferred embodiments from about 70 µg to about 7000 µg per day per subject, and preferably from about 2100 µg to 3500 µg per day per subject.

The term "pharmaceutically acceptable salts" refers to salts prepared from pharmaceutically acceptable non-toxic acids including inorganic acids and organic acids. Optionally, ester analogues of S(−) amlodipine may be used in the present invention.

Since the compound of the present invention is basic, salts may be prepared from pharmaceutically acceptable non-toxic acids including inorganic and organic acids. Such acids include acetic, benzene-sulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. Particularly preferred are besylate, hydrobromic, hydrochloric, phosphoric and sulfuric acids.

The invention is further defined by reference to the following examples describing in detail the testing and preparation of the compositions of the present invention. It will be apparent to those skilled in the art, that many modifications, both to materials and methods, may be practiced without departing from the purpose and interest of this invention.

EXAMPLES $^3$H-Amlodipine Binding In Vitro

Radiolabeled dihydropyridine calcium channel antagonists such as $^3$H-amlodipine are selective ligands for a drug receptor site associated with the voltage-dependent calcium channel. A constant concentration of the radioligand $^3$H-amlodipine (0.3–0.4 nM) is incubated with increasing concentrations of a non-labeled test drug (0.1 nM-1 mM) in the presence of plasma membranes from bovine cerebral cortices. If the test drug exhibits any affinity to calcium channels, it is able to compete with the radioligand for channel binding sites. Thus, the lower the concentration range of the test drug, in which the competition reaction occurs, the more potent is the test drug.

Procedure

Materials and Solutions preparation buffer: Tris-HCl 50 mM pH 7.4 incubation buffer: Tris-HCl 50 mM Genapol 0.001 % pH 7.4 radioligand: $^3$H-amlodipine specific activity approximately 2.0–3.25 TBq/mmol (50–87 Ci/mmol) for inhibition of $^3$H-amlodipine binding in non-specific binding experiments: nifedipine (Sigma)

Two freshly-slaughtered bovine brains are obtained from the slaughter house and placed in ice-cold preparation buffer. In the laboratory, approx. 5 g wet weight of the two frontal cerebral cortices are separated from the brains.

Membrane Preparation

The tissue is homogenized (glass Teflon potter) in ice-cold preparation buffer, corresponding to 1 g cerebral wet weight/ 50 ml buffer, and centrifuged at 48.000xg (4° C.) for 10 min. The resulting pellets are resuspended in approx. 270 ml preparation buffer, and the homogenate is centrifuged as before. The final pellets are dissolved in preparation buffer, corresponding to 1 g cerebral cortex wet weight/30 ml buffer. The membrane suspension is immediately stored in aliquots of 5–10 ml at −77° C. Protein content of the membrane suspension is determined according to the method of Lowry et al (1951) with bovine serum albumin as a standard.

At the day of the experiment, the required volume of the membrane suspension is slowly thawed and centrifuged at 48.000×g (4° C.) for 10 min. The resulting pellets are resuspended in a volume of ice-cold incubation buffer, yielding a membrane suspension with a protein content of 0.6–0.8 mg/ml. After homogenization (glass Teflon potter), the membrane suspension is stirred under cooling for 20–30 min until the start of the experiment.

Experimental Course

As 1,4-dihydropyridines tend to bind to plastic material, all dilution steps are done in glass tubes. For each concentration samples are prepared in triplicate. The total volume of each incubation sample is 200 ml (microtiter plates).

Saturation Experiments total binding:
- 50 µl $^3$H-amlodipine (12 concentrations, $5 \times 10^{-11}$–$4 \times 10^{-9}$ M)
- 50 µl incubation buffer non-specific-binding:
- 50 µl $^3$H-amlodipine (4 concentrations, $5 \times 10^{-11}$–$4 \times 10^{-9}$ M)
- 50 µl nifedipine ($5 \times 10^{-7}$ M)

Competition Experiments
- 50 µl $^3$H-amlodipine (1 constant concentration, 3–4 × $10^{-10}$ M)
- 50 µl incubation buffer without or with non-labeled test drug (15 concentrations, $10^{-10}$–$10_{-3}$ M)

The binding reaction is started by adding 100 µl membrane suspension per incubation sample (0.6–0.8 mg protein/ml). The samples are incubated for 60 min in a bath shaker at 25° C. The reaction is stopped by subjecting the total incubation volume to rapid vacuum filtration over glass fiber filters. Thereby the membrane-bound is separated from the free radioactivity. Filters are washed immediately with approx. 20 ml ice-cold rinse buffer per sample.

The retained membrane-bound radioactivity on the filter is measured after addition of 2 ml liquid scintillation cocktail per sample in a liquid scintillation counter.

Evaluation

The following parameters are calculated:
total binding
non-specific binding
specific binding=total binding–non-specific binding The dissociation constant (Ki) of the test drug is determined from the competition experiment of $^3$H-amlodipine versus non-labeled drug by a computer-supported analysis of the binding data.

$IC_{50}$=concentration of the test drug, which displaces 50 % of specifically bound $^3$H-amlodipine in the competition experiment

[$^3$H]=concentration of $^3$H-amlodipine in the competition experiment.

$K_D^3$H=dissociation constant of $^3$H-amlodipine, determined from the saturation experiment.

$$Ki = \frac{K_p^3H \times IC_{50}}{K_D^3H + [^3H]}$$

The Ki-value of the test drug is the concentration, at which 50 % of the receptors are occupied by the test drug.

The affinity constant Ki [mol/l] is recorded and serves as a parameter to assess the efficacy of the test drug.

Standard data: nifedipine Ki=$2$–$4 \times 10^{-9}$ mol/l

References

Barhanin J, Borsotto M, Coppola T, Fosset M, Hosey MM, Mourre C, Pauron D, Qar J, Romey G, Schmid A, Vandaele S, Van Renterghem C, Lazdunski M (1989) Biochemistry, molecular pharmacology, and functional control of Ca 2+-channels. In: Wray DW, Norman RI, Hess P (eds) Calcium Channels: Structure and Function. Ann NY Acad Sci 560: 15–26

Bean BP (1989) Classes of calcium channels in vertebrate cells. Annu Rev Physiol 51:367–384

Bertolino M, Llinas RR (1992) The central role of voltage-activated and receptor-operated calcium channels in neuronal cells. Annu Rev Pharmacol Toxicol 32:399–421

Catterall WA, Saegar MJ, Takahashi M, Nunoki K (1989) Molecular properties of dihydropyridine-sensitive calcium channels. In: Wray DW, Norman RI, Hess P (eds) Calcium Channels: Structure and Function. Ann NY Acad Sci 560: 1–14

Dascal N (1990) Analysis and functional characteristics of di-hydropyridine-sensitive and -insensitive calcium channel proteins. Biochem Pharmacol 40:1171–1178

Dolphin AC (1991) Regulation of calcium channel activity by GTP binding proteins and second messengers. Biochim Biophys Acta 1091:68–80

Ferrante J Triggle DJ (1990) Drug- and disease-induced regulation of voltage-dependent calcium channels. Pharmacol Rev 42:29–44

Fleckenstein A (1964) Die Bedeutung der energiereichen Phosphate fur Kontraktilitat und Tonus des Myocards. Verh Dtsch Ges Inn Med 70:81–99

Fleckenstein A (1983) History of calcium antagonists. Circ Res 52 (Suppl I):3–16

Fleckenstein A, Frey M, Fleckenstein-Grün G (1983) Consequences of uncontrolled calcium entry and its prevention with calcium antagonists. Eur Heart J 4 (Suppl H):43–50

Fleckenstein A, Frey M, Fleckenstein-Grün G (1986) Antihypertensive and arterial anticalcinotic effects of calcium an-tagonists. Am J Cardiol 57:1 D--10D Fleckenstein A, Kammermeier H, Döring HJ, Freund HJ (1967) Zum Wirkungsmechanismus neuartiger Koronardilatatoren mit gleichzeitig Sauerstoffeinsparenden Myocardeffekten, Prenylamin, Irpoveratril. Z Kreislaufforsch 56 :716–744, 839–853

Galizzi JP, Quar J, Fosset M, Van Renterghem C, Lazdunski M (1987) Regulation of calcium channels in aortic muscle cells by protein kinase C activators (diacylglycerol and phorbol esters) and by peptides (vasopressin and bombesin) that stimulate phosphoinositide breakdown. J Biol Chem 262:6947–6950

Hosey MM, Chang FC, O'Callahan CM, Ptasienski J (1989) L- type channels in cardiac and skeletal muscle: purification and phosphorylation. In: Wray DW, Norman RI, Hess P (eds) Calcium Channels: Structure and Function. Ann NY Acad Sci 560:27–38

Maggi CA, Tramontana M, Cecconi R, Santicioli P (1990) Neurochemical evidence of N-type calcium channels in transmitter secretion from peripheral nerve endings of sensory nerves in guinea pigs. Neurosci Lett 114:203–206

Mintz IM, Adams ME, Bean BP (1992) P-Type calcium channels in rat central and peripheral neurons. Neuron 9:85–95

Moresco RM, Govoni S, Battaini F, Trivulzio S, Trabucchi M (1990) Omegaconotoxin binding decreases in aged rat brain. Neurobiol Aging 11:433–436

Nakao SI, Ebata H, Hamamoto T, Kagawa Y, Hirata H (1988) Solubilization and reconstitution of voltage-dependent calcium channel from bovine cardiac muscle. Ca2+ influx assay using the fluorescent dye Quin2. Biochim Biophys Acta 944:337–343

Porzig (1990) Pharmacological modulation of voltage-dependent calcium channels in intact cells. Rev Physiol Biochem Pharmacol 114:209–262

Rampe D, Triggle DJ (1993) New synthetic ligands for L-type voltage-gated calcium channels. Progr Drug Res 40:191–238

Reuter H, Porzig H, Kokubun S, Prod'Hom B (1988) Calcium channels in the heart. Properties and modulation by dihydropyridine enantiomers. Ann NY Acad Sci 522:16–24

Rosenberg RL, Isaacson JS, Tsien RW (1989) Solubilization, partial purification, and properties of ω-conotoxin receptors associated with voltage-dependent calcium channels. In: Wray DW, Norman RI, Hess P (eds) Calcium Channels: Structure and Function. Ann NY Acad Sci 560:39–52

Spedding M, Paoletti R (1992) Classification of calcium channels and the sites of action of drugs modifying channel function. Pharmacol Rev 44:363–376

Tsien RW, Tsien RY (1990) Calcium channels, stores and oscillations. Annu Rev Cell Biol 6:715–760

What is claimed is:

1. A method for blocking calcium channels, while avoiding the concomitant liability of adverse effects associated with administration of racemic amlodipine, which comprises administering to an animal in need of calcium channel blocking therapy, an amount of deuterated S(−) amlodipine, or a pharmaceutically acceptable salt thereof, substantially free of its R(+) stereoisomer, wherein the deuterated S(−) amlodipine or salt thereof, comprises an amlodipine selected from the genus described by:

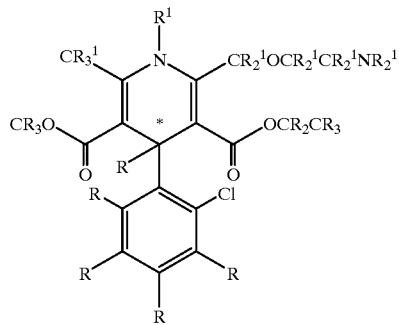

(II)

wherein R represents either hydrogen or deuterium, and at least one R is deuterium; and wherein $R^1$ represents either hydrogen or deuterium, and at least one $R^1$ is deuterium, said amount being sufficient to provide calcium channel blockade but insufficient to cause said adverse effects of racemic amlodipine.

2. A compound comprising deuterated S(−) amlodipine, or a pharmaceutically acceptable salt thereof, substantially free of the R(+) stereoisomer, wherein the deuterated S(−) amlodipine or salt thereof, comprises an amlodipine selected from the genus described by:

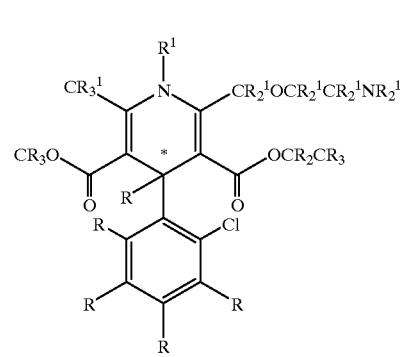

(II)

wherein R represents either hydrogen or deuterium, and at least one R is deuterium; and wherein $R^1$ represents either hydrogen or deuterium, and at least one $R^1$ is deuterium.

3. The method of claim 1 wherein the therapeutic indication for calcium channel blockade is a member selected from the group consisting of hypertension, angina, cerebral ischemia, cerebral disorders, arrhythmias, cardiac hypertropy, heart failure, coronary vasospasm, myocardial infarction, renal impairment, viral infection, thrombosis, atherosclerosis, peripheral vascular disease, migraine headache, restenosis following vascular surgery or injury and acute renal failure.

4. A pharmaceutical composition comprising the compound of claim 2 and a pharmaceutically acceptable carrier.

* * * * *